(12) United States Patent
Hossainy et al.

(10) Patent No.: US 7,591,841 B2
(45) Date of Patent: Sep. 22, 2009

(54) IMPLANTABLE DEVICES FOR ACCELERATED HEALING

(75) Inventors: Syed Faiyaz Ahmed Hossainy, Fremont, CA (US); Florian Niklas Ludwig, Mountain View, CA (US); David Gale, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 395 days.

(21) Appl. No.: 11/303,724

(22) Filed: Dec. 16, 2005

(65) Prior Publication Data

US 2008/0160061 A1    Jul. 3, 2008

(51) Int. Cl.
  *A61F 2/06*    (2006.01)
  *A61K 38/17*   (2006.01)
(52) U.S. Cl. .................. 623/1.1; 530/353; 530/356; 623/1.42; 623/1.47; 623/1.48; 623/1.15
(58) Field of Classification Search .................. None
  See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |

(Continued)

FOREIGN PATENT DOCUMENTS

DE    42 24 401    1/1994

(Continued)

OTHER PUBLICATIONS

International Search Rep. for PCT/US2006/047677, filed Dec. 13, 2006, mailed Jan. 17, 2008, 14 pgs.

(Continued)

*Primary Examiner*—Suzanne M. Noakes
(74) *Attorney, Agent, or Firm*—Squire, Sanders & Dempsey L.L.P.

(57) ABSTRACT

Implantable devices (e.g., stent) having a protein patterning or bioactive patterning for accelerated healing and method of forming and using the same are provided.

14 Claims, No Drawings

U.S. PATENT DOCUMENTS

| | | | |
|---|---|---|---|
| 5,721,131 A | 2/1998 | Rudolph et al. | |
| 5,723,219 A | 3/1998 | Kolluri et al. | |
| 5,728,152 A * | 3/1998 | Mirsch et al. ................ 623/2.1 | |
| 5,735,897 A | 4/1998 | Buirge | |
| 5,746,998 A | 5/1998 | Torchilin et al. | |
| 5,759,205 A | 6/1998 | Valentini | |
| 5,776,184 A | 7/1998 | Tuch | |
| 5,783,657 A | 7/1998 | Pavlin et al. | |
| 5,788,979 A | 8/1998 | Alt et al. | |
| 5,800,392 A | 9/1998 | Racchini | |
| 5,820,917 A | 10/1998 | Tuch | |
| 5,824,048 A | 10/1998 | Tuch | |
| 5,824,049 A | 10/1998 | Ragheb et al. | |
| 5,830,178 A | 11/1998 | Jones et al. | |
| 5,837,008 A | 11/1998 | Berg et al. | |
| 5,837,313 A | 11/1998 | Ding et al. | |
| 5,849,859 A | 12/1998 | Acemoglu | |
| 5,851,508 A | 12/1998 | Greff et al. | |
| 5,854,376 A | 12/1998 | Higashi | |
| 5,857,998 A | 1/1999 | Barry | |
| 5,858,746 A | 1/1999 | Hubbell et al. | |
| 5,865,814 A | 2/1999 | Tuch | |
| 5,869,127 A | 2/1999 | Zhong | |
| 5,873,904 A | 2/1999 | Ragheb et al. | |
| 5,876,433 A | 3/1999 | Lunn | |
| 5,877,224 A | 3/1999 | Brocchini et al. | |
| 5,879,713 A | 3/1999 | Roth et al. | |
| 5,902,875 A | 5/1999 | Roby et al. | |
| 5,905,168 A | 5/1999 | Dos Santos et al. | |
| 5,910,564 A | 6/1999 | Gruning et al. | |
| 5,914,387 A | 6/1999 | Roby et al. | |
| 5,919,893 A | 7/1999 | Roby et al. | |
| 5,925,720 A | 7/1999 | Kataoka et al. | |
| 5,932,299 A | 8/1999 | Katoot | |
| 5,955,509 A | 9/1999 | Webber et al. | |
| 5,958,385 A | 9/1999 | Tondeur et al. | |
| 5,962,138 A | 10/1999 | Kolluri et al. | |
| 5,971,954 A | 10/1999 | Conway et al. | |
| 5,980,928 A | 11/1999 | Terry | |
| 5,980,972 A | 11/1999 | Ding | |
| 5,997,517 A | 12/1999 | Whitbourne | |
| 6,010,530 A | 1/2000 | Goicoechea | |
| 6,011,125 A | 1/2000 | Lohmeijer et al. | |
| 6,015,541 A | 1/2000 | Greff et al. | |
| 6,033,582 A | 3/2000 | Lee et al. | |
| 6,034,204 A | 3/2000 | Mohr et al. | |
| 6,042,875 A | 3/2000 | Ding et al. | |
| 6,051,576 A | 4/2000 | Ashton et al. | |
| 6,051,648 A | 4/2000 | Rhee et al. | |
| 6,054,553 A | 4/2000 | Groth et al. | |
| 6,056,993 A | 5/2000 | Leidner et al. | |
| 6,060,451 A | 5/2000 | DiMaio et al. | |
| 6,060,518 A | 5/2000 | Kabanov et al. | |
| 6,080,488 A | 6/2000 | Hostettler et al. | |
| 6,096,070 A | 8/2000 | Ragheb et al. | |
| 6,099,562 A | 8/2000 | Ding et al. | |
| 6,110,188 A | 8/2000 | Narciso, Jr. | |
| 6,110,483 A | 8/2000 | Whitbourne et al. | |
| 6,113,629 A | 9/2000 | Ken | |
| 6,120,491 A | 9/2000 | Kohn et al. | |
| 6,120,536 A | 9/2000 | Ding et al. | |
| 6,120,788 A | 9/2000 | Barrows | |
| 6,120,904 A | 9/2000 | Hostettler et al. | |
| 6,121,027 A | 9/2000 | Clapper et al. | |
| 6,129,761 A | 10/2000 | Hubbell | |
| 6,136,333 A | 10/2000 | Cohn et al. | |
| 6,143,354 A | 11/2000 | Koulik et al. | |
| 6,153,252 A | 11/2000 | Hossainy et al. | |
| 6,159,978 A | 12/2000 | Myers et al. | |
| 6,165,212 A | 12/2000 | Dereume et al. | |
| 6,172,167 B1 | 1/2001 | Stapert et al. | |
| 6,177,523 B1 | 1/2001 | Reich et al. | |
| 6,180,632 B1 | 1/2001 | Myers et al. | |
| 6,203,551 B1 | 3/2001 | Wu | |
| 6,211,249 B1 | 4/2001 | Cohn et al. | |
| 6,214,901 B1 | 4/2001 | Chudzik et al. | |
| 6,231,600 B1 | 5/2001 | Zhong | |
| 6,240,616 B1 | 6/2001 | Yan | |
| 6,245,753 B1 | 6/2001 | Byun et al. | |
| 6,245,760 B1 | 6/2001 | He et al. | |
| 6,248,129 B1 | 6/2001 | Froix | |
| 6,251,136 B1 | 6/2001 | Guruwaiya et al. | |
| 6,254,632 B1 | 7/2001 | Wu et al. | |
| 6,258,121 B1 | 7/2001 | Yang et al. | |
| 6,258,371 B1 | 7/2001 | Koulik et al. | |
| 6,262,034 B1 | 7/2001 | Mathiowitz et al. | |
| 6,270,788 B1 | 8/2001 | Koulik et al. | |
| 6,277,449 B1 | 8/2001 | Kolluri et al. | |
| 6,283,947 B1 | 9/2001 | Mirzaee | |
| 6,283,949 B1 | 9/2001 | Roorda | |
| 6,284,305 B1 | 9/2001 | Ding et al. | |
| 6,287,628 B1 | 9/2001 | Hossainy et al. | |
| 6,299,604 B1 | 10/2001 | Ragheb et al. | |
| 6,306,176 B1 | 10/2001 | Whitbourne | |
| 6,331,313 B1 | 12/2001 | Wong et al. | |
| 6,335,029 B1 | 1/2002 | Kamath et al. | |
| 6,344,035 B1 | 2/2002 | Chudzik et al. | |
| 6,346,110 B2 | 2/2002 | Wu | |
| 6,358,556 B1 | 3/2002 | Ding et al. | |
| 6,379,381 B1 | 4/2002 | Hossainy et al. | |
| 6,387,379 B1 | 5/2002 | Goldberg et al. | |
| 6,395,326 B1 | 5/2002 | Castro et al. | |
| 6,419,692 B1 | 7/2002 | Yang et al. | |
| 6,451,373 B1 | 9/2002 | Hossainy et al. | |
| 6,475,779 B2 | 11/2002 | Mathiowitz et al. | |
| 6,482,834 B2 | 11/2002 | Spada et al. | |
| 6,494,862 B1 | 12/2002 | Ray et al. | |
| 6,503,538 B1 | 1/2003 | Chu et al. | |
| 6,503,556 B2 | 1/2003 | Harish et al. | |
| 6,503,954 B1 | 1/2003 | Bhat et al. | |
| 6,506,437 B1 | 1/2003 | Harish et al. | |
| 6,524,347 B1 | 2/2003 | Myers et al. | |
| 6,527,801 B1 | 3/2003 | Dutta | |
| 6,527,863 B1 | 3/2003 | Pacetti et al. | |
| 6,528,526 B1 | 3/2003 | Myers et al. | |
| 6,530,950 B1 | 3/2003 | Alvarado et al. | |
| 6,530,951 B1 | 3/2003 | Bates et al. | |
| 6,540,776 B2 | 4/2003 | Sanders Millare et al. | |
| 6,544,223 B1 | 4/2003 | Kokish | |
| 6,544,543 B1 | 4/2003 | Mandrusov et al. | |
| 6,544,582 B1 | 4/2003 | Yoe | |
| 6,555,157 B1 | 4/2003 | Hossainy | |
| 6,558,733 B1 | 5/2003 | Hossainy et al. | |
| 6,565,659 B1 | 5/2003 | Pacetti et al. | |
| 6,572,644 B1 | 6/2003 | Moein | |
| 6,585,755 B2 | 7/2003 | Jackson et al. | |
| 6,585,765 B1 | 7/2003 | Hossainy et al. | |
| 6,585,926 B1 | 7/2003 | Mirzaee | |
| 6,605,154 B1 | 8/2003 | Villareal | |
| 6,613,432 B2 | 9/2003 | Zamora et al. | |
| 6,616,765 B1 | 9/2003 | Hossainy et al. | |
| 6,620,617 B2 | 9/2003 | Mathiowitz et al. | |
| 6,623,448 B2 | 9/2003 | Slater | |
| 6,625,486 B2 | 9/2003 | Lundkvist et al. | |
| 6,641,611 B2 | 11/2003 | Jayaraman | |
| 6,645,135 B1 | 11/2003 | Bhat | |
| 6,645,195 B1 | 11/2003 | Bhat et al. | |
| 6,656,216 B1 | 12/2003 | Hossainy et al. | |
| 6,656,506 B1 | 12/2003 | Wu et al. | |
| 6,660,034 B1 | 12/2003 | Mandrusov et al. | |
| 6,663,662 B2 | 12/2003 | Pacetti et al. | |
| 6,663,880 B1 | 12/2003 | Roorda et al. | |
| 6,666,880 B1 | 12/2003 | Chiu et al. | |
| 6,673,154 B1 | 1/2004 | Pacetti et al. | |

| Patent No. | Date | Inventor |
|---|---|---|
| 6,673,385 B1 | 1/2004 | Ding et al. |
| 6,689,099 B2 | 2/2004 | Mirzaee |
| 6,689,350 B2 | 2/2004 | Uhrich |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,776,796 B2 | 8/2004 | Falotico et al. |
| 6,780,424 B2 | 8/2004 | Claude |
| 6,790,228 B2 | 9/2004 | Hossainy et al. |
| 6,824,559 B2 | 11/2004 | Michal |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,890,583 B2 | 5/2005 | Chudzik et al. |
| 6,899,731 B2 | 5/2005 | Li et al. |
| 7,008,667 B2 | 3/2006 | Chudzik et al. |
| 2001/0007083 A1 | 7/2001 | Roorda |
| 2001/0029351 A1 | 10/2001 | Falotico et al. |
| 2001/0037145 A1 | 11/2001 | Guruwaiya et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0051730 A1 | 5/2002 | Bodnar et al. |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0111590 A1 | 8/2002 | Davila et al. |
| 2002/0160036 A1 | 10/2002 | Geistlich et al. |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0170685 A1 | 9/2004 | Carpenter et al. |
| 2004/0170752 A1 | 9/2004 | Luthra et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0100951 A1 | 5/2005 | Pircher |
| 2005/0106210 A1 | 5/2005 | Ding et al. |
| 2005/0113903 A1 | 5/2005 | Rosenthal et al. |
| 2007/0003589 A1 | 1/2007 | Astafieva et al. |
| 2007/0050007 A1* | 3/2007 | Kondyurin et al. ......... 623/1.13 |
| 2007/0100323 A1* | 5/2007 | Ludwig et al. ............ 604/509 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 088 564 | 4/2001 |
| EP | 1 192 957 | 4/2002 |
| EP | 1 273 314 | 1/2003 |

| | | |
|---|---|---|
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/26162 | 4/2002 |
| WO | WO 02/34307 | 5/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/065881 | 8/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

U.S. Appl. No. 09/835,429, filed Apr. 16, 2001, Wu et al.
U.S. Appl. No. 10/871,658, filed Jun. 18, 2004, Hossainy et al.
Anonymous, *Cardiologists Draw—Up The Dream Stent*, Clinica 710:15 (Jun. 17, 1996), http://www.dialogweb.com/cgi/document?reg=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).
Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Gombotz et al., *Biodegradable Polymers for Protein and Peptide Drug Delivery*, Bioconjugate Chem. 6: 332-351 (1995).
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Kipshidze et al., *Role of the Endothelium in Modulating Neointimal Formation*, J. of the Am. Coll. of Cardiology vol. 44, No. 4 (2004).
Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Lutolf et al., *Synthesis and Physicochemical Characterization of End-Linked Poly(ethylene glycol)-co-peptide Hydrogels Formed by Michael-Type Addition*, Biomacromolecules 4: 713-722 (2003).
Marconi et al., *Covalent bonding of heparin to a vinyl copolymer for biomedical applications*, Biomaterials 18(12):885-890 (1997).
Matsumaru et al., *Embolic Materials For Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).
Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Serruys et al., *A Randomized Comparison of the Value of Additional Stenting After Optimal Balloon Angioplasty for Long Coronary Lesions*, J. of the Am. Coll. Of Cardiology vol. 39, No. 3, (2002).

Shigeno, *Prevention of Cerebrovascular Spasm By Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

IMPLANTABLE DEVICES FOR ACCELERATED HEALING

BACKGROUND

1. Field of the Invention

This invention is directed to protein patterning on implantable devices, such as drug delivery vascular stents, for accelerated healing.

2. Description of the State of the Art

Percutaneous coronary intervention (PCI) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

The introduction of drug delivery stents has reduced the incidence of in-stent restenosis (ISR) after PCI (see, e.g., Serruys, P. W., et al., J.Am.Coll.Cardiol. 39:393-399 (2002)), which has represented the Achilles heel of interventional cardiology for more than one decade. However, ISR still poses a significant problem given the large volume of coronary interventions and expanding indications. The pathophysiology of ISR constitutes a complex interaction between cellular and acellular elements of the vessel wall and the blood. The loss of endothelial integrity after PCI constitutes a major factor for the development of ISR (see, e.g., Kipshidze, N., et al., J.Am.Coil.Cardiol. 44:733-739 (2004)).

The embodiments of the present invention address these concerns as well as others that are apparent by one having ordinary skill in the art.

SUMMARY

Provided herein is an implantable device that includes a protein patterning or a bioactive patterning that contains a protein and an agent selected from an adhesion molecule including an RGD motif, a chemo-attractant of an endothelial cell, a NO releasing or generating material or agent, an agent that promotes endothelialization, or combinations thereof. The protein patterning or bioactive patterning can further include a bioactive agent. Some exemplary bioactive agents include, but are not limited to, paclitaxel, docetaxel, estradiol, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl rapamycin, and 40-O-tetrazole-rapamycin, 40-epi-(N1-tetrazolyl)-rapamycin (ABT-578), clobetasol, corticosteroids, prodrugs thereof, co-drugs thereof, or combinations thereof.

The device having features described herein can be implanted in a patient to treat, prevent, ameliorate, or reduce a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or heart valve dysfunction such as heart valve re-gurgitation. In some embodiments, the device can be implanted in a patient for pro-healing of the disorder.

DETAILED DESCRIPTION

Provided herein is an implantable device that includes a protein patterning or a bioactive patterning that contains a protein and an agent that can be an adhesion molecule including an RGD motif, a chemo-attractant of an endothelial cell, a NO releasing or generating material or agent, an agent that promotes endothelialization, or combinations thereof. The protein patterning or bioactive patterning can further include a bioactive agent.

Some exemplary bioactive agents include, but are not limited to, paclitaxel, docetaxel, estradiol, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, corticosteroids, prodrugs thereof, co-drugs thereof, or combinations thereof.

In some embodiments, the adhesion molecule can be an RGD peptide, a cRGD peptide, RGD mimetics, peptides or proteins containing the RGD sequence, structural or functional equivalents thereof, or combinations thereof. The RGD or RGD mimetics described herein includes any peptides or peptide mimetics result from the modification of the cyclic Arg-Gly-Asp peptide. The modification can be on the pendant groups and/or on the backbone of the peptide. Peptide synthesis, including the synthesis of peptide mimetics, is well documented and can be readily achieved via, for example, combinatorial chemistry.

The device having features described herein can be implanted in a patient to treat, prevent, ameliorate, or reduce a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or heart valve dysfunction such as heart valve regurgitation. In some embodiments, the device can be implanted in a patient for pro-healing of the disorder. As used herein, the term pro-healing refers to promoting the healing of a disorder.

Protein Patterning

In some embodiments, the implantable device provided herein includes a protein patterning. The protein patterning includes a protein that can be, for example, fibronectin, laminin 5, elastin, silk elastin, collagen or a peptide.

In some embodiments, the protein patterning can be negative imprints of cell adhesion molecules on the surface. The adhesion molecule can be, e.g., RGD, cRGD, RGD mimetics, peptides or proteins containing the RGD sequence, structural or functional equivalents thereof, or combinations thereof. The surface can be a metallic surface, a polymeric surface, or a coating surface. In some embodiments, the protein patterning can include a chemo-attractant for endothelial cells other than RGD.

In some embodiments, the protein patterning can include a pro-healing material or matrix such as nitric oxide (NO) donors, hyaluronic acid or fragments thereof, glycosaminoglycan or fragments thereof, endothelial progenitor cell (EPC) capturing antibody, or combinations thereof.

In some embodiments, the protein patterning can include a bioactive agent that promotes endothelialization (as known as pro-endothelialization), such as vascular endothelial growth factor (VEGF), platelet-derived growth factor (PDGF), fibroblast growth factor (FGF), placenta derived growth factor (PlGF), or combinations thereof. The growth factors can be blended with other components of the protein patterning or negative imprint or in some embodiments, can be conjugated to the surface by ionic interaction, hydrogen bonding and/or chemical bonding (with or without a spacer) to localize their effect.

The protein patterning can be carried out by methods known in the art of gene chips and other biochips (see, e.g., U.S. application Publication No. 20050100951). For example, protein patterning can be formed by lithography and rubber-stamping methods, nano-droplet deposition by contact transfer, surface patterning by AFM material transfer, reactive microcontact printing by, for example, functionalizing the surface of a device followed by microstamping of the reactive biological ligands, self-assembling of the proteins, ink jet technologies as described in U.S. application Ser. No. 09/835,429, etc. In some embodiments, patterning can be done by patterning underlying substrate surface or coating surface, e.g., by providing localized functional areas for attachment of protein layer(s), or by locally modifying surface hydrophobicity/hydrophilicity. Functional areas generally contain functional groups attached on the surface. Such functional groups include, e.g., carboxyl groups, hydroxyl groups, thiol groups, amino groups, aldehyde groups, and other groups commonly used for attaching a protein to a polymeric or non-polymeric surface. In some embodiments, the surface can be modified to have different hydrophobicity/hydrophilicity.

The protein patterning can be tuned and controlled by a variety of factors. Such factors include, for example, the composition of the protein layer adsorbed on the surface, physicochemical structure of the adsorbed protein layer, such as denatured state, natural state, tertiary state, epitope unfolding state, etc., patterned surface characteristics (e.g., ratio of surface subjected to patterning, surface area subjected to patterning, and density of patterning per unit area), relative shape and regional distribution of the pattern on the surface of the device, texture parameters such as porosity or roughness factor, and/or depth profile of the protein pattern.

Bioactive Patterning

In some embodiments, the implantable device described herein includes a bioactive patterning. The bioactive patterning contains a plurality of pores on the surface of the device and/or the coating of the device. The pores can have a size ranging from, e.g., about 1 μm to about 2000 μm, about 10 μm to about 1000 μm, about 10 μm to about 500 μm, about 10 to about 200 μm, about 10 μm to about 100 μm, about 10 μm to about 100 μm, about 30 μm to about 100 μm, or about 30 μm to about 50 μm.

The porosity can vary in size and shape in part of or throughout the device. One of ordinary skill in the art can readily create a pattern of porosity according to the design of the device. For example, in some embodiments, pores may be localized near surface or transverse stent struts or both, depending on location within the stent. The pores located on the edges and/or surface of the struts may enhance the rate of cell engulfment while the pore volume of the strut may enhance the permeation rate of EC (endothelial cell) and smooth muscle cell (SMC) in a controlled manner.

In some embodiments, the areas of porous device and/or coating can be selectively or completely loaded with a protein and an agent, depending upon the design of the device.

In some embodiments, the protein can be, for example, fibronectin, laminin 5, elastin, silk elastin, collagen or a peptide. The agent can be an adhesion molecule including an RGD motif, a chemo-attractant of an endothelial cell, a NO releasing or generating material or agent, an agent that promotes endothelialization, or combinations thereof.

In some embodiments, the pores of the device can be loaded with an adhesion molecule that includes an RGD motif. In some embodiments, the adhesion molecule can be, e.g., RGD, cRGD, RGD mimetics, peptides or proteins containing the RGD sequence, structural or functional equivalents thereof, or combinations thereof.

The porosity on the device or in the coating can be achieved by techniques known in the art, for example, blow molding, porogen leaching, or locally melting polymer with heated needle, etc. for a device formed of a polymeric material (e.g., poly(lactic acid) (PLA), polypropylene (PP), poly(L-lactide-co-trimethylene carbonate), or poly(desamino tyrosyl-tyrosine ethyl ester carbonate) (poly(DTE carbonate)) and mechanical, e-beam or laser drilling for devices formed of a polymeric material or a non-metallic material such as a metallic stent, with or without a polymeric coating. In-some embodiments, the porosity of the implantable device can be created by making the device from a composite of electrospun fibers.

In some embodiments, the porosity can be created by photochemical etching, polymer droplet deposition (e.g., from melted polymer spray), or partial and patterned enzymatic degradation. In some other embodiments, the porosity can be created by spray coating with a solution including a porogen such as an inorganic or organic salt (e.g., sodium chloride), lactose, dextrose or other water soluble species, active drug (e.g., everolimus) and a biocompatible polymer and then leaching the porogen from the surface layer. By this leaching methodology, one can create a porous surface layer without compromising the mechanical integrity of the device.

In some embodiments, the bioactive patterning can include a chemo-attractant for endothelial cells other than RGD.

Chemo-Attractants Other Than RGD

As used herein, the chemo-attractant includes any synthetic or natural molecules capable of attracting endothelial cells. The attractant generally have a degree of selectivity towards endothelial cells. The chemo-attractant includes any synthetic or natural molecules capable of binding to adhesion receptors differentially expressed on the endothelial cells. One such adhesion receptor can be integrin. Some exemplary chemo-attractants include, but are not limited to, small integrin binding molecules and small molecules binding to other adhesion receptors differentially expressed on the endothelial cells.

In some embodiments, the chemo-attractant can be any molecules capable of binding to ICAM (intercellular adhesion molecule) molecules and/or VCAM (vascular cell adhesion molecule) molecules, which are present in the endothelial cells. In some embodiments, such chemo-attractant can be, for example, receptors binding to ICAM or VCAM on endothelial cells. Such include receptors include, but are not limited to, Decoy receptor 3 (DcR3), which is a tumor necrosis factor (TNF) that preferentially binds to ICAM and VCAM, β_2 integrin LFA-1 (LFA-1Af) (expressed on lymphocytes) which has conformational changes in extracellular domains enabling higher affinity binding to the ligand ICAM-1, and combinations thereof.

In some embodiments, the chemo-attractant can be used in an encapsulated form, e.g., encapsulation in liposome or another material such as a biodegradable polymer. The encapsulated chemo-attractant can be used in connection with a catheter and then be released therefrom.

Biocompatible Polymers

In some embodiments, the protein patterning or bioactive patterning can include one or more biocompatible polymers. The device, such as the stent, can be coated with these polymers or the device itself can be made from these polymers. The biocompatible polymer can be biodegradable (both bioerodable or bioabsorbable) or nondegradable and can be hydrophilic or hydrophobic.

Representative biocompatible polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide/poly(lactic acid) (PEO/PLA)), polyalkylene oxides such as poly(ethylene oxide), poly(propylene oxide), poly (ether ester), polyalkylene oxalates, polyphosphazenes, phosphoryl choline, choline, poly(aspirin), polymers and copolymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof. In some embodiments, the copolymer described herein can exclude any one of the aforementioned polymers.

As used herein, the terms poly(D,L-lactide), poly(L-lactide), poly(D,L-lactide-co-glycolide), and poly(L-lactide-co-glycolide) can be used interchangeably with the terms poly(D,L-lactic acid), poly(L-lactic acid), poly(D,L-lactic acid-co-glycolic acid), or poly(L-lactic acid-co-glycolic acid), respectively.

Linkers

In some embodiments, the RGD, RGD mimetics, the chemo-attractant, the NO releasing or generating agent, or the agent that promotes endothelialization described herein can be attached to the protein or a polymer matrix in the protein patterning or bioactive patterning described herein via a labile linker or via physical interactions such as interpenetrating networking. The labile linker can be a linker sensitive to stimuli. For example, the linker can be a hydrolytically degradable linker or an enzymetically degradable linker.

Hydrolytically degradable linkers degrade under physiological condition in the presence of water. A hydrolytically degradable linker links the chemo-attractant and the polymer via the linker's reactive groups. For example, in some embodiments, the linker can be an amino acid grouping that includes amino, thiol, and/or carboxylic groups. Some exemplary strategies for forming hydrolytically degradable linkers include:

(1) ε-Amino group of lysine (which can be integrated into a polymer) and α-amino group of a protein. The amine can be on the polymer backbone (with or without a spacer (PEG, alkyl chain)). This yields an amide, thiourea, alkylamine or urethane linkage.

(2) Thiol group or a free cysteine, which forms a thioether linkage.

(3) Thiol group on a cysteine, which can be conjugated with vinylsulfone ($R-SO_2-CH=CH_2$).

(4) Carboxylic acid groups on the aspartic and glutamic acid.

Some examples of hydrolytically degradable linkages include amide linkages that can be generated by reacting an amine group with succinate esters such as N-hydroxysuccinimide (NHS), thiol linkages such as disulfide (R-L1-S—S-L2-R') where the length of the linker L1 and L2 control the hydrolization, or ester bonds formed by coupling the peptide's carboxylic terminus with a hydroxyl on the polymer backbone (with or without a spacer (PEG, alkyl chain)). Esterification can be carried out using established methods in the art (e.g., carbodiimide chemistry in the presence of 1-ethyl-3-(3-dimethylaminopropyl)carbodiimide (EDC)).

Enzymatically degradable linkers/linkages are degraded by an enzyme, often to target a specific area of the body or organ. For example, a specific dipeptide sequence can be incorporated into the linker, which can be cleaved by an enzyme. Some examples of enzymetically degradable linkers or linkages include, but are not limited to, self-immolative p-aminobenzyloxycarbonyl (PABC) spacer between the dipeptide and the polymer, dipeptides such as phenylaniline-lysine and valine-cysteine, or PEG/dipeptide linkages such as alanyl-valine, alanyl-proline and glycyl-proline.

Some other linker/linkages can be found at "Biodegradable Polymers for Protein and Peptide Drug Delivery" Bioconjugate Chem. 1995, 6:332-351; M. P. Lutolf and J. A. Hubbell, Biomacromolecules 2003, 4:713-722; and U.S. patent application Ser. No. 10/871,658. Some additional representative linking chemistry is described in U.S. patent application Ser. No. 10/871,658, now issued as U.S. Pat. No. 7,563,780.

Bioactive Agents

In some embodiments, the protein patterning or bioactive patterning described herein can optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents, agents that promote the healing of the endothelium other than NO releasing or generating agents (generators), or agents that promote the attachment, migration and proliferation of endothelial cells (CNP) while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, corticosteroids or combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Biobeneficial Material

In some embodiments, the protein patterning or bioactive patterning described herein can optionally include a biobeneficial material. The combination can be mixed, blended, or patterned in separate layers. The biobeneficial material useful in the coatings described herein can be a polymeric material or non-polymeric material. The biobeneficial material is preferably non-toxic, non-antigenic and non-immunogenic. A biobeneficial material is one which enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly(ether-esters), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, chitosan, alginate, silicones, PolyActive™, and combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

EXAMPLES OF IMPLANTABLE DEVICE

As used herein, an implantable device can be any suitable medical substrate that can be implanted in a human or veterinary patient. Examples of such implantable devices include self-expandable stents, balloon-expandable stents, stent-grafts, grafts (e.g., aortic grafts), heart valve prosthesis (e.g., artificial heart valves) or vascular graft, cerebrospinal fluid shunts, pacemaker electrodes, catheters, and endocardial leads (e.g., FINELINE and ENDOTAK, available from Guidant Corporation, Santa Clara, Calif.), devices facilitating anastomosis such as anastomotic connectors. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a protein patterning or bioactive patterning can be formed on an implantable device or prosthesis, e.g., a stent. For a device including one or more active agents, the agent will retain on the device such as a stent during delivery and expansion of the device, and released at a desired rate and for a predetermined duration of time at the site of implantation.

Preferably, the device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device comprising a protein patterning on said device, wherein the protein patterning comprises:
 (a) a protein selected from the group consisting of fibronectin, laminin 5, elastin, silk elastin, collagen and combinations thereof, and
 (b) an agent selected from the group consisting of an adhesion molecule that includes a RGD motif, a chemoattractant of an endothelial cell, a NO releasing or generating agent, an agent that promotes endothelialization, or combinations thereof;
 and wherein the protein of (a) and the agent of (b) are chemically bonded to one another via a spacer.

2. The implantable device of claim 1, wherein the adhesion molecule is selected from the group consisting of an RGD peptide, a cRGD peptide, RGD mimetics, peptides or proteins containing the RGD sequence, and combinations thereof.

3. The implantable device of claim 1, wherein the protein is in a state selected from the group consisting of denatured state, natural state, tertiary state, and epitope unfolding state.

4. The implantable device of claim 1, further comprising a material or compound selected from the group consisting of hyaluronic acid, glycosaminoglycan, endothelial progenitor cell capturing antibody, and combinations thereof.

5. The implantable device of claim 1, wherein the agent that promotes endothelialization is a growth factor selected from the group consisting of VEGF, PDGF, FGF, PlGF, and combinations thereof.

6. The implantable device of claim 5, wherein the growth factor is chemically conjugated to the surface of the implantable device or a coating on the device.

7. The implantable device of claim 1, further comprising a biocompatible polymer.

8. The implantable device of claim 1, wherein the protein patterning is formed on a surface selected from the group consisting of a local functionalized area comprising functional groups, a local hydrophilic area, a locally hydrophobic area, and a combination thereof.

9. The implantable device of claim 1, wherein the spacer is poly(ethylene glycol) (PEG).

10. The implantable device of claim 1, further comprising a bioactive agent selected from the group consisting of paclitaxel, docetaxel, estradiol, super oxide dismutases, super oxide dismutases mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy) ethyl-rapamycin (everolimus), 40-O-(3-hydroxy)propyl-rapamycin, 40-O-[2-(2-hydroxy) ethoxy]ethyl-rapamycin, and 40-O-tetrazole-rapamycin, 40-epi-(N1-tetrazolyl)-rapamycin (ABT-578), corticosteroids, clobetasol, pimecrolimus, imatinib mesylate, midostaurin, prodrugs thereof, co-drugs thereof, and a combination thereof.

11. The implantable device of claim 1, wherein the protein patterning is in the form of negative imprints.

12. The implantable device of claim 1, which is a stent.

13. The implantable device of claim 1, which is an absorbable stent.

14. The implantable device of claim 1, which is a heart valve prosthesis or vascular graft.

* * * * *

UNITED STATES PATENT AND TRADEMARK OFFICE
CERTIFICATE OF CORRECTION

PATENT NO. : 7,591,841 B2  Page 1 of 1
APPLICATION NO. : 11/303724
DATED : September 22, 2009
INVENTOR(S) : Hossainy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 492 days.

Signed and Sealed this

Fourteenth Day of December, 2010

David J. Kappos
*Director of the United States Patent and Trademark Office*